(12) United States Patent
Zheng et al.

(10) Patent No.: US 7,592,313 B2
(45) Date of Patent: Sep. 22, 2009

(54) METHOD OF STIMULATING PROLIFERATION OF REGULATORY T CELLS IN A DIABETIC MAMMAL

(75) Inventors: Guoxing Zheng, Rockford, IL (US); Aoshuang Chen, Rockford, IL (US)

(73) Assignee: Board of Trustees of the University of Illinois, Urbana, IL (US)

( * ) Notice: Subject to any disclaimer, the term of this patent is extended or adjusted under 35 U.S.C. 154(b) by 49 days.

(21) Appl. No.: 11/596,706

(22) PCT Filed: May 12, 2005

(86) PCT No.: PCT/US2005/016665

§ 371 (c)(1),
(2), (4) Date: Jul. 27, 2007

(87) PCT Pub. No.: WO2005/124346

PCT Pub. Date: Dec. 29, 2005

(65) Prior Publication Data

US 2007/0292431 A1    Dec. 20, 2007

Related U.S. Application Data

(60) Provisional application No. 60/571,520, filed on May 17, 2004.

(51) Int. Cl.
*A61K 38/16* (2006.01)
*C07K 14/705* (2006.01)

(52) U.S. Cl. ............... 514/12; 424/134.1; 530/350; 530/387.3

(58) Field of Classification Search ............... None
See application file for complete search history.

(56) References Cited

U.S. PATENT DOCUMENTS

2003/0223989 A1* 12/2003 Pluenneke ............... 424/131.1
2004/0109847 A1*  6/2004 Chen et al. ................ 424/85.4

OTHER PUBLICATIONS

Xia et al., Blood; Nov. 16, 2003, vol. 102, No. 11, pp. 946a-947a.*
Xu et al., Gene Therapy, 2005, 12: 1526-1533.*
Kwon et al., Exp. Mol. Med., 2003, 35: 8-16.*
Saouli et al., J. Exp. Med., 187: 1849-1862.*
Xia et al Tracking Mechanisms of Infused Alloantigen-Specific CD4+CD25+ and CD8+CD25+ Regulatory T Cells during In Vivo Lethal Acute GVHD Prevention. Blood, Nov. 16, 2003, vol. 102, No. 11, pp. 946a, see Abstract #3526 in its entirety.

* cited by examiner

*Primary Examiner*—Ilia Ouspenski
(74) *Attorney, Agent, or Firm*—Banner & Witcoff, Ltd.

(57) ABSTRACT

The thymus-derived $CD4^+CD25^+$ T cells belong to a subset of regulatory T cells potentially capable of suppressing the proliferation of pathogenic effector T cells. Intriguingly, these suppressor cells are themselves anergic, proliferating poorly to mitogenic stimulation in culture. The inventors have found that the 4-1BB co-stimulator receptor, best known for promoting the proliferation and survival of $CD8^+$ T cells, also induces the proliferation of the $CD4^+CD25^+$ regulatory T cells both in culture and in vivo. The proliferating $CD4^+CD25^+$ T cells produce no detectable IL-2, suggesting that 4-1BB costimulation of these cells does not involve IL-2 production. The 4-1BB-expanded $CD4^+CD25^+$ T cells are functional, as they remain suppressive to other T cells in co-culture. These results support the notion that the peripheral expansion of the $CD4^+CD25^+$ T cells is controlled in part by co-stimulation.

10 Claims, 8 Drawing Sheets

SEQUENCE LISTING

<160> NUMBER OF SEQ ID NOS: 8

<210> SEQ ID NO 1
<211> LENGTH: 254
<212> TYPE: PRT
<213> ORGANISM: Homo sapiens

<400> SEQUENCE: 1

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Cys Ala Val Phe
            35                  40                  45

Leu Ala Cys Pro Trp Ala Val Ser Gly Ala Arg Ala Ser Pro Gly Ser
        50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 2
<211> LENGTH: 762
<212> TYPE: DNA
<213> ORGANISM: Homo sapiens

<400> SEQUENCE: 2
atggaatacg cctctgacgc ttcactggac cccgaagccc cgtggcctcc cgcgccccgc      60
gctcgcgcct gccgcgtact gccttgggcc ctggtcgcgg ggctgctgct gctgctgctg     120
ctcgctgccg cctgcgccgt cttcctcgcc tgcccctggg ccgtgtccgg ggctcgcgcc     180
tcgcccggct ccgcggccag cccgagactc cgcgagggtc ccgagctttc gcccgacgat     240
cccgccggcc tcttggacct gcggcagggc atgtttgcgc agctggtggc caaaatgtt      300 ctgctgatcg atgggcccct gagctggtac agtgacccag gcctggcagg cgtgtccctg     360

```
acgggggggcc tgagctacaa agaggacacg aaggagctgg tggtggccaa ggctggagtc    420
tactatgtct tctttcaact agagctgcgg cgcgtggtgg ccggcgaggg ctcaggctcc    480
gtttcacttg cgctgcacct gcagccactg cgctctgctg ctggggccgc cgccctggct    540
ttgaccgtgg acctgccacc cgcctcctcc gaggctcgga actcggcctt cggtttccag    600
ggccgcttgc tgcacctgag tgccggccag cgcctgggcg tccatcttca cactgaggcc    660
agggcacgcc atgcctggca gcttacccag ggcgccacag tcttgggact cttccgggtg    720 accccccgaaa tcccagccgg actcccttca ccgaggtcgg aa                     762
```

<210> SEQ ID NO 3
<211> LENGTH: 309
<212> TYPE: PRT
<213> ORGANISM: Mus musculus

<400> SEQUENCE: 3

```
Met Asp Gln His Thr Leu Asp Val Glu Asp Thr Ala Asp Ala Arg His
 1               5                  10                  15

Pro Ala Gly Thr Ser Cys Pro Ser Asp Ala Ala Leu Leu Arg Asp Thr
             20                  25                  30

Gly Leu Leu Ala Asp Ala Ala Leu Ser Asp Thr Val Arg Pro Thr
         35                  40                  45

Asn Ala Ala Leu Pro Thr Asp Ala Ala Tyr Pro Ala Val Asn Val Arg
     50                  55                  60

Asp Arg Glu Ala Ala Trp Pro Ala Leu Asn Phe Cys Ser Arg His
 65                  70                  75                  80

Pro Lys Leu Tyr Gly Leu Val Ala Leu Val Leu Leu Leu Ile Ala
                 85                  90                  95

Ala Cys Val Pro Ile Phe Thr Arg Thr Glu Pro Arg Pro Ala Leu Thr
            100                 105                 110

Ile Thr Thr Ser Pro Asn Leu Gly Thr Arg Glu Asn Asn Ala Asp Gln
            115                 120                 125

Val Thr Pro Val Ser His Ile Gly Cys Pro Asn Thr Thr Gln Gln Gly
        130                 135                 140

Ser Pro Val Phe Ala Lys Leu Leu Ala Lys Asn Gln Ala Ser Leu Cys
145                 150                 155                 160

Asn Thr Thr Leu Asn Trp His Ser Gln Asp Gly Ala Gly Ser Ser Tyr
                165                 170                 175

Leu Ser Gln Gly Leu Arg Tyr Glu Glu Asp Lys Lys Glu Leu Val Val
            180                 185                 190

Asp Ser Pro Gly Leu Tyr Tyr Val Phe Leu Glu Leu Lys Leu Ser Pro
        195                 200                 205

Thr Phe Thr Asn Thr Gly His Lys Val Gln Gly Trp Val Ser Leu Val
    210                 215                 220

Leu Gln Ala Lys Pro Gln Val Asp Asp Phe Asp Asn Leu Ala Leu Thr
225                 230                 235                 240

Val Glu Leu Phe Pro Cys Ser Met Glu Asn Lys Leu Val Asp Arg Ser
                245                 250                 255

Trp Ser Gln Leu Leu Leu Lys Ala Gly His Arg Leu Ser Val Gly
            260                 265                 270

Leu Arg Ala Tyr Leu His Gly Ala Gln Asp Ala Tyr Arg Asp Trp Glu
        275                 280                 285

Leu Ser Tyr Pro Asn Thr Thr Ser Phe Gly Leu Phe Leu Val Lys Pro
    290                 295                 300
```

Asp Asn Pro Trp Glu
305

<210> SEQ ID NO 4
<211> LENGTH: 927
<212> TYPE: DNA
<213> ORGANISM: Mus musculus

<400> SEQUENCE: 4

| | | | | | |
|---|---|---|---|---|---|
| atggaccagc | acacacttga | tgtggaggat | accgcggatg | ccagacatcc agcaggtact | 60 |
| tcgtgcccct | cggatgcggc | gctcctcaga | gataccgggc | tcctcgcgga cgctgcgctc | 120 |
| ctctcagata | ctgtgcgccc | cacaaatgcc | gcgctcccca | cggatgctgc ctaccctgcg | 180 |
| gttaatgttc | gggatcgcga | ggccgcgtgg | ccgcctgcac | tgaacttctg ttcccgccac | 240 |
| ccaaagctct | atggcctagt | cgctttggtt | ttgctgcttc | tgatcgccgc ctgtgttcct | 300 |
| atcttcaccc | gcaccgagcc | tcggccagcg | ctcacaatca | ccacctcgcc caacctgggt | 360 |
| acccgagaga | ataatgcaga | ccaggtcacc | ctgtttccc | acattggctg ccccaacact | 420 |
| acacaacagg | gctctcctgt | gttcgccaag | ctactggcta | aaaaccaagc atcgttgtgc | 480 |
| aatacaactc | tgaactggca | cagccaagat | ggagctggga | gctcatacct atctcaaggt | 540 |
| ctgaggtacg | aagaagacaa | aaaggagttg | gtggtagaca | gtcccgggct ctactacgta | 600 |
| ttttggaac | tgaagctcag | tccaacattc | acaaacacag | gccacaaggt gcagggctgg | 660 |
| gtctctcttg | ttttgcaagc | aaagcctcag | gtagatgact | tgacaacttt ggccctgaca | 720 |
| gtggaactgt | tcccttgctc | catggagaac | aagttagtgg | accgttcctg gagtcaactg | 780 |
| ttgctcctga | aggctggcca | ccgcctcagt | gtgggtctga | ggcttatct gcatggagcc | 840 |
| caggatgcat | acagagactg | ggagctgtct | tatcccaaca | ccaccagctt tggactcttt | 900 |
| cttgtgaaac | ccgacaaccc | atgggaa | | | 927 |

<210> SEQ ID NO 5
<211> LENGTH: 32
<212> TYPE: DNA
<213> ORGANISM: Mus musculus

<400> SEQUENCE: 5
gtgccacgcc tcgagcgcac cgagcctcgg cc                                        32

<210> SEQ ID NO 6
<211> LENGTH: 31
<212> TYPE: DNA
<213> ORGANISM: Mus musculus

<400> SEQUENCE: 6
tactggatcc tcattcccat gggttgtcgg g                                         31

<210> SEQ ID NO 7
<211> LENGTH: 618
<212> TYPE: DNA
<213> ORGANISM: Mus musculus

<400> SEQUENCE: 7

| | | | | | |
|---|---|---|---|---|---|
| cgcaccgagc | tcggccagc | gctcacaatc | accacctcgc | ccaacctggg tacccgagag | 60 |
| aataatgcag | accaggtcac | ccctgtttcc | cacattggct | gccccaacac tacacaacag | 120 |
| ggctctcctg | tgttcgccaa | gctactggct | aaaaaccaag | catcgttgtg caatacaact | 180 |
| ctgaactggc | acagccaaga | tggagctggg | agctcatacc | tatctcaagg tctgaggtac | 240 |

```
gaagaagaca aaaaggagtt ggtggtagac agtcccgggc tctactacgt atttttggaa    300
ctgaagctca gtccaacatt cacaaacaca ggccacaagg tgcagggctg ggtctctctt    360
gttttgcaag caaagcctca ggtagatgac tttgacaact tggccctgac agtggaactg    420
ttcccttgct ccatggagaa caagttagtg gaccgttcct ggagtcaact gttgctcctg    480
aaggctggcc accgcctcag tgtgggtctg agggcttatc tgcatggagc ccaggatgca    540
tacagagact gggagctgtc ttatcccaac accaccagct ttggactctt tcttgtgaaa    600
cccgacaacc catgggaa                                                  618
```

<210> SEQ ID NO 8
<211> LENGTH: 206
<212> TYPE: PRT
<213> ORGANISM: Mus musculus

<400> SEQUENCE: 8

```
Arg Thr Glu Pro Arg Pro Ala Leu Thr Ile Thr Thr Ser Pro Asn Leu
 1               5                  10                  15

Gly Thr Arg Glu Asn Asn Ala Asp Gln Val Thr Pro Val Ser His Ile
            20                  25                  30

Gly Cys Pro Asn Thr Thr Gln Gln Gly Ser Pro Val Phe Ala Lys Leu
        35                  40                  45

Leu Ala Lys Asn Gln Ala Ser Leu Cys Asn Thr Thr Leu Asn Trp His
 50                  55                  60

Ser Gln Asp Gly Ala Gly Ser Ser Tyr Leu Ser Gln Gly Leu Arg Tyr
 65                  70                  75                  80

Glu Glu Asp Lys Lys Glu Leu Val Val Asp Ser Pro Gly Leu Tyr Tyr
                85                  90                  95

Val Phe Leu Glu Leu Lys Leu Ser Pro Thr Phe Thr Asn Thr Gly His
                100                 105                 110

Lys Val Gln Gly Trp Val Ser Leu Val Leu Gln Ala Lys Pro Gln Val
                115                 120                 125

Asp Asp Phe Asp Asn Leu Ala Leu Thr Val Glu Leu Phe Pro Cys Ser
 130                 135                 140

Met Glu Asn Lys Leu Val Asp Arg Ser Trp Ser Gln Leu Leu Leu Leu
145                 150                 155                 160

Lys Ala Gly His Arg Leu Ser Val Gly Leu Arg Ala Tyr Leu His Gly
                165                 170                 175

Ala Gln Asp Ala Tyr Arg Asp Trp Glu Leu Ser Tyr Pro Asn Thr Thr
                180                 185                 190

Ser Phe Gly Leu Phe Leu Val Lys Pro Asp Asn Pro Trp Glu
                195                 200                 205
```

METHOD OF STIMULATING PROLIFERATION OF REGULATORY T CELLS IN A DIABETIC MAMMAL

This invention was made using funds from the U.S. government, National Institutes of Health Grant CA92243. The government therefore retains certain rights in the invention.

TECHNICAL FIELD OF THE INVENTION

This invention is related to the area of immunology. In particular, it relates to regulation of CD4+CD25+ regulatory T cells.

BACKGROUND OF THE INVENTION

The immune system operates on the principle of checks and balances. For T cells, there is evidence that their activities may be controlled in part by subsets of T cells specialized in regulation. The thymic-derived CD4+CD25+ T cells belong to one of these subsets. Unlike conventional T cells that function as effector cells during an immune reaction, the CD4+CD25+ T cells act to suppress the activation of conventional T cells and in doing so, actively maintain immunologic tolerance in the periphery (reviewed in references[1-3]). Recent studies indicate that the CD4+CD25+ T cells may play important roles in the prevention of certain auto-immune and allo-immune diseases[4-11].

Given the importance of these regulatory cells, it is critical to understand the mechanisms controlling their activation and expansion in the periphery. Intriguingly, freshly isolated CD4+CD25+ T cells are anergic, proliferating poorly in response to TCR stimulation in vitro. How these cells expand in vivo in response to physiological stimuli has yet to be determined. Recently it has been shown that CD4+CD25+ T cells carrying a transgenic TCR can undergo clonal expansion in vivo in response to immunization with a specific antigen, and that the dynamics of the regulatory cell population depends largely on local environment[12-14]. In addition to antigen presentation, co-stimulation by activated dendritic cells (DC) is likely to be a key factor affecting the dynamics of CD4+CD25+ T cells proliferation, as it has been shown that the CD4+CD25+ T cells can be expanded in vivo with bone marrow-derived, antigen-presenting DC, in a manner that is dependent on B7 expression[14]. Interestingly, deficiency in B7 only reduces, but does not entirely eliminate, the potency of DC, suggesting that additional co-stimulators other than B7 may also play a role[14]. Such a role of additional co-stimulators is consistent with previous evidence that the development of IL-10-secreting, respiratory regulatory T cells depends on ICOS, not B7[15].

4-1BB (CD137) is a membrane receptor protein of the TNFR superfamily. Like CD28, 4-1BB is a potent co-stimulator, known to promote CD4+ and CD8+ T cell activation and survival (reviewed in reference[16]). Unlike CD28, which competes for B7 with another receptor, CTLA-4[17], 4-1BB binds monogamously to a single ligand, 4-1BBL, thereby allowing more straightforward determination. Furthermore, previous studies have indicated that 4-1BB gene expression is upregulated in CD4+CD25+ T cells[18, 19].

There is a continuing need in the art for methods of obtaining CD4+CD25+ T cells and overcoming their anergy. If reasonable amounts of CD4+CD25+ T cells were available, they could be used inter alia for drug screening and therapy of immune-related diseases.

SUMMARY OF THE INVENTION

A first embodiment of the invention provides a method of stimulating the proliferation of CD4+CD25+ regulatory T cells. One or more CD4+CD25+ regulatory T cells are contacted in vitro with an effective amount of soluble 4-1BBL. Proliferation of the cell(s) is thereby stimulated, forming an expanded CD4+CD25+ regulatory T cell population.

A second embodiment of the invention provides a kit for testing candidate therapeutic agents. The kit contains an in vitro expanded population of CD4+CD25+ regulatory T cells. It also contains a plurality of identical vessels.

A third embodiment of the invention provides a method for testing substances as candidate therapeutic agents. A test substance is contacted with an in vitro expanded population of CD4+CD25+ regulatory T cells. The proliferative index of the population is determined. A test substance is identified as a candidate therapeutic agent if the test substance increases the proliferative index relative to a control population which has not been contacted with a test substance.

According to another aspect of the invention a method of stimulating the proliferation of CD4+CD25+ regulatory T cells in a mammal is provided. An effective amount of soluble 4-1BBL is administered to a mammal in need of immune suppression or immune toleration. Proliferation of CD4+CD25+ regulatory T cells is thereby stimulated.

Another aspect of the invention is another method of stimulating the proliferation of CD4+CD25+ regulatory T cells. CD4+CD25+ regulatory T cells are contacted in vitro with an effective amount of reagent cells comprising 4-1BBL-Fc on their surfaces. Proliferation of said CD4+CD25+ regulatory T cells is thereby stimulated.

Another embodiment of the invention provides another method of stimulating the proliferation of CD4+CD25+ regulatory T cells in a mammal. An effective amount of reagent cells comprising 4-1BBL-Fc on their surfaces is administered to a mammal in need of immune suppression or immune toleration. Proliferation of CD4+CD25+ regulatory T cells is thereby stimulated.

Still another embodiment of the invention is an isolated population of reagent cells for stimulating CD4+CD25+ regulatory T cells. The reagent cells comprise 4-1BBL-Fc and OX40L-Fc on their surfaces.

An additional embodiment of the invention is an isolated population of reagent cells for stimulating CD4+CD25+ regulatory T cells. The reagent cells comprise 4-1BBL-Fc and ICOSL-Fc on their surfaces.

Yet another embodiment of the invention is an isolated population of reagent cells for stimulating CD4+CD25+ regulatory T cells, The reagent cells comprise 4-1BBL-Fc and anti-CD3 monoclonal antibody on their surfaces.

These and other embodiments, which will be apparent to those of skill in the art upon reading the specification, provide the art with reagents and methods for tolerizing or suppressing immune responses.

BRIEF DESCRIPTION OF THE DRAWINGS

(FIGS. 1A-C) Freshly-isolated bulk spleen cells were depleted of MHC II+ cells by magnet cell sorting (Miltenyi Biotec) and stained with biotin-conjugated anti-CD25 mAb/APC-conjugated streptavidin, FITC-conjugated anti-CD4 mAb, and a specific reagent for 4-1BB, in the presence of anti-CD16/CD32 mAb as Fc blocker. The stained cells were analyzed for 4-1BB expression by multi-color flow cytometry. (FIG. 1A) CD4$^+$CD25$^-$ and CD4$^+$CD25$^+$ cells were identified and gated. (FIG. 1B) Comparative analysis of 4-1BB-specific signals from the two gated cell populations of BALB/c origin. The cells were stained with either PE-conjugated anti-4-1BB mAb (top) or 4-1BBL-Fc/PE-conjugated goat anti-human Fc$_\gamma$ Ab (bottom). (FIG. 1C) Similar analysis of 4-1BB-specific signals in gated cells of DO11.10 origin. The cells were stained with PE-conjugated anti-4-1BB mAb. (FIG. 1D) 4-1BB staining of activated BALB/c CD4$^+$CD25$^-$ and CD4$^+$CD25$^+$ T cells. Purified BALB/c splenic CD4$^+$CD25$^+$ and CD4$^+$CD25$^-$ T cells were stimulated, respectively, in culture for two days with plate-bound anti-CD3 mAb (bound at 8 μg/ml) and murine IL-2 (100 U/ml). The cells were stained with PE-conjugated anti-4-1BB mAb and analyzed by flow cytometry. Solid line, 4-1BB-specific staining; dashed line, isotype-matched control staining. Data in each panel are representative of two or three independent experiments.

(FIG. 2A) PRO-IAd cells, non-painted (dashed line) or painted with 30 μg/ml of 4-1BBL-Fc (solid line), were stained with PE-conjugated anti-mouse 4-1BBL mAb and analyzed by flow cytometry. (FIG. 2B) CD4+CD25+ T cells were stimulated with plate-bound anti-CD3 mAb (bound at 8 μg/ml) and PRO-IAd cells, either non-painted or painted with indicated Fc protein, in the absence or presence of anti-4-1BB blocking mAb (5 μg per well). The cells were pulsed with 1 μCi of 3H-thymidine per well at 48 h and harvested at 64 h; 3H-thymidine incorporation was then determined. Data are representative of three independent experiments.

(FIGS. 4A & 4B) Donor cell population (CD4 and KJ1-26 double positive, circled) was identified and gated on as a small fraction of total CD4$^+$ T cells. (FIGS. 4C & 4D) Proliferation (decrement of CFSE fluorescence) and death (7-AAD positive stain) of the gated cells were analyzed by quadrant plots. Cell counts in each quadrant are indicated. Data are representative of three independent experiments. The increased counts of proliferating cells (lower left quadrant) produced in the 4-1BBL-Fc-treated groups (FIG. 4D), as compared to the counts produced in the control-treated groups (FIG. 4C), is statistically significant by one-tailed Student t test (p<0.01).

DETAILED DESCRIPTION OF THE INVENTION

Figures 1A, 1B, 1C, 1D:
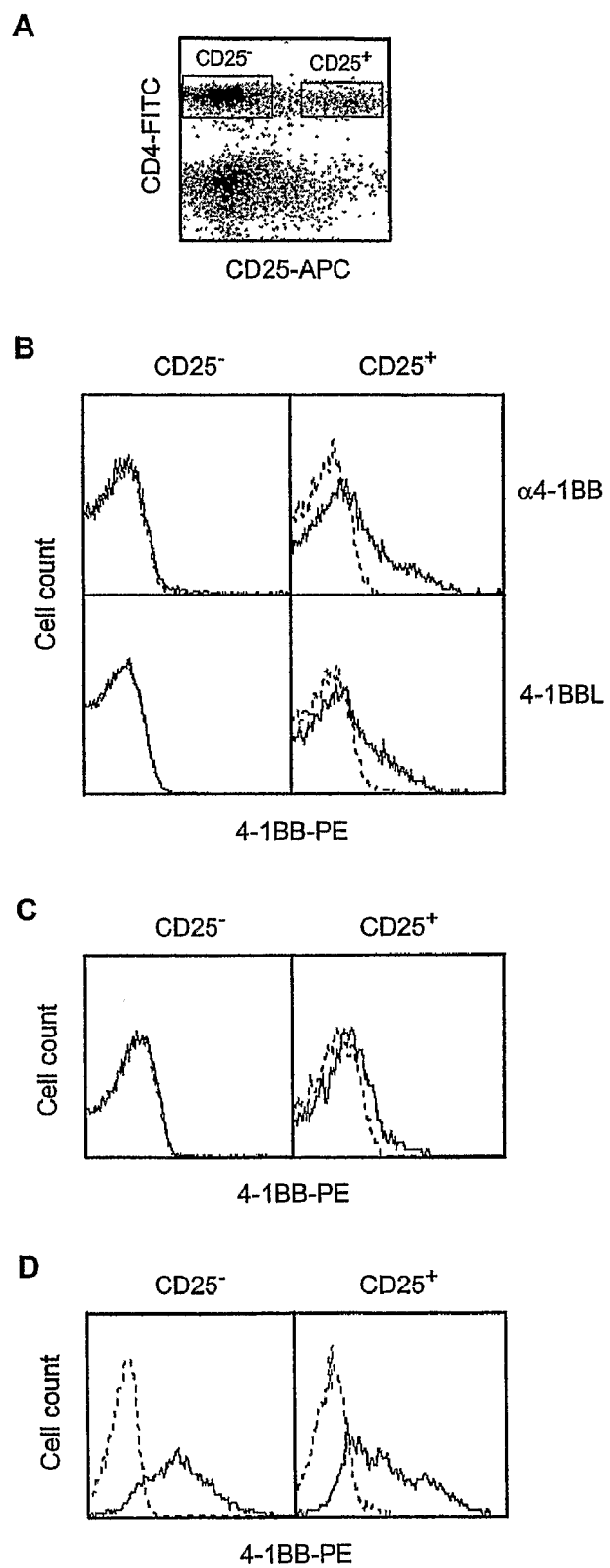
FIGS. 1A-1D. demonstrate that the 4-1BB receptor was present on CD4+CD25+ T cells.

It is a discovery of the present inventors that freshly isolated CD4$^+$CD25$^+$ T cells constitutively express low levels of the 4-1BB receptor protein at the cell surface and that the signaling of this receptor by 4-1BBL can significantly augment the proliferation of these cells in culture and in vivo. In addition, the 4-1BB-expanded cells remain suppressive to other T cells. Hence, 4-1BB plays a role in the expansion of functional CD4$^+$CD25$^+$ T cells.

A proliferative index is a measurement of the proliferation of cells. This can be measured by any means known in the art. For example, cells can be tested at different times to measure the rate of incorporation of various metabolites, such as nucleotides, amino, acids, sugars, etc., into macromolecules. Cells can be simply counted at different times to observe an increase in cell or colony number. Any means known in the art for determining the rate of proliferation of a population of cells can be used.

Stimulatory molecules according to the present invention are any that engage the 4-1BB receptor molecule and cause it to signal other cellular components resulting in cellular proliferation. The 4-1BB ligand (4-1BBL) can be used in a soluble form, in a dimeric form attached to an immunoglobulin Fc region, or attached to a cell surface, such as an antigen presenting cell. A protein form or a nucleotide encoding the protein form may be delivered to the CD4+CD25+ T cells. The ligand can be from the same species as the cells to maximize activity and minimize adverse antigenic events. One such ligand is a human ligand having the sequence:

(SEQ ID NO: 1)
MEYASDASLDPEAPWPPAPRARACRVLPWALVAGLLLLLLLAAACAVFLA
CPWAVSGARASPGSAASPRLREGPELSPDDPAGLLDLRQGMFAQLVAQNV
LLIDGPLSWYSDPGLAGVSLTGGLSYKEDTKELVVAKAGVYYVFFQLELR
RVVAGEGSGSVSLALHLQPLRSAAGAAALALTVDLPPASSEARNSAFGFQ
GRLLHLSAGQRLGVHLHTEARARHAWQLTQGATVLGLFRVTPEIPAGLPS
PRSE.

A polynucleotide encoding this ligand may have any of the possible sequences which encode it. One such sequence is:

(SEQ ID NO: 2)
ATGGAATACGCCTCTGACGCTTCACTGGACCCCGAAGCCCCGTGGCCTCC
CGCGCCCCGCGCTCGCGCCTGCCGCGTACTGCCTTGGGCCCTGGTCGCGG
GGCTGCTGCTGCTGCTGCTGCTCGCTGCCGCCTGCGCCGTCTTCCTCGCC
TGCCCCTGGGCCGTGTCCGGGGCTCGCGCCTCGCCCGGCTCCGCGGCCAG
CCCGAGACTCCGCGAGGGTCCCGAGCTTTCGCCCGACGATCCCGCCGGCC
TCTTGGACCTGCGCCAGGGCATGTTTGCGCAGCTGGTGGCCCAAAATGTT
CTGCTGATCGATGGCCCCTGAGCTGGTACAGTGACCCAGGCCTGGCAGG
CGTGTCCCTGACGGGGGCCTGAGCTACAAAGAGGACACGAAGGAGCTG
GTGGTGGCCAAGGCTGGAGTCTACTATGTCTTCTTTCAACTAGAGCTGCG
GCGCGTGGTGGCCGGCGAGGGCTCAGGCTCCGTTTCACTTGCGCTGCACC
TGCAGCCACTGCGCTCTGCTGCTGGGGCCGCCGCCCTGGCTTTGACCGTG
GACCTGCCACCCGCCTCCTCCGAGGCTCGGAACTCGGCCTTCGGTTTCCA
GGGCCGCTTGCTGCACCTGAGTGCCGGCCAGCGCCTGGGCGTCCATCTTC
ACACTGAGGCCAGGGCACGCCATGCCTGGCAGCTTACCCAGGGCGCCAC
AGTCTTGGGACTCTTCCGGGTGACCCCCGAAATCCCAGCCGGACTCCCTT
CACCGAGGTCGGAA.

A murine form of the protein has a sequence:

(SEQ ID NO: 3)
MDQHTLDVEDTADARHPAGTSCPSDAALLRDTGLLADAALSDTVRPTNAA
LPTDAAYPAVNVRDREAAWPPALNFCSRHPKLYGLVALVLLLLIAACVPI
FTRTEPRPALTITTSPNLGTRENNADQVTPVSHIGCPNTTQQGSPVFAKL
LAKNQASLCNTTLNWHSQDGAGSSYLSQGLRYEEDKKELVVDSPGLYYVF
LELKLSPTFTNTGHKVQGWVSLVLQAKPQVDDFDNLALTVELFPCSMENK
LVDRSWSQLLLLKAGHRLSVGLRAYLHGAQDAYRDWELSYPNTTSFGLFL
VKPDNPWE.

It can be encoded by a DNA sequence:

(SEQ ID NO: 4)
ATGGACCAGCACACACTTGATGTGGAGGATACCGCGGATGCCAGACATCC
AGCAGGTACTTCGTGCCCCTCGGATGCGGCGCTCCTCAGAGATACCGGGC
TCCTCGCGGACGCTGCGCTCCTCTCAGATACTGTGCGCCCCACAAATGCC
GCGCTCCCCACGGATGCTGCCTACCCTGCGGTTAATGTTCGGGATCGCGA
GGCCGCGTGGCCGCCTGCACTGAACTTCTGTTCCCGCCACCCAAAGCTCT
ATGGCCTAGTCGCTTTGGTTTTGCTGCTTCTGATCGCCGCCTGTGTTCCT
ATCTTCACCCGCACCGAGCCTCGGCCAGCGCTCACAATCACCACCTCGCC
CAACCTGGGTACCCGAGAGAATAATGCAGACCAGGTCACCCCTGTTTCCC
ACATTGGCTGCCCCAACACTACACAACAGGGCTCTCCTGTGTTCGCCAAG
CTACTGGCTAAAAACCAAGCATCGTTGTGCAATACAACTCTGAACTGGCA
CAGCCAAGATGGAGCTGGGAGCTCATACCTATCTCAAGGTCTGAGGTACG
AAGAAGACAAAAAGGAGTTGGTGGTAGACAGTCCCGGGCTCTACTACGTA
TTTTTGGAACTGAAGCTCAGTCCAACATTCACAAACACAGGCCACAAGGT
GCAGGGCTGGGTCTCTCTTGTTTTGCAAGCAAAGCCTCAGGTAGATGACT
TTGACAACTTGGCCCTGACAGTGGAACTGTTCCCTTGCTCCATGGAGAAC
AAGTTAGTGGACCGTTCCTGGAGTCAACTGTTGCTCCTGAAGGCTGGCCA
CCGCCTCAGTGTGGGTCTGAGGGCTTATCTGCATGGAGCCCAGGATGCAT
ACAGAGACTGGGAGCTGTCTTATCCCAACACCACCAGCTTTGGACTCTTT
CTTGTGAAACCCGACAACCCATGGGAA

Allelic variants can be used as well. The criterion for suitable protein molecules is that they effectively signal CD4+CD25+ regulatory T cells via the 4-1BB receptor.

Regulatory T cells can be isolated by use of antibodies specific for the CD4 and CD25 cell surface antigens. Any technique can be used including immunoaffinity chromatography, fluorescence activated cell sorting (FACS), immunoprecipitation, etc. Single regulatory T cells can be obtained by dilution or dividing of a population of such cells to an extent that at least some of the subpopulations (aliquots) have a single cell in them. Some of the subpopulations may have more and some may have less. After expansion, subpopulations that started from a single cell will be homogeneous or monoclonal. Homogeneity can be determined by determination of cell surface markers, for example. The FACS technique can be useful in this determination.

Packaging for cells which have been expanded can be in a divided or undivided container or vessel. Undivided vessels include bottles, flasks, tubes, etc. Divided vessels include assemblies of multiple cuvettes or tubes, microtiter plates, divided Petri dishes, etc. Vessels may be insulated to maintain a desired lower than ambient temperature during shipment. Dry ice, wet ice, or liquid nitrogen may be used to maintain a lower than ambient temperature for preservation of cell viability. Cells may be frozen or lyophilized for storage or shipment. Techniques for storing and shipping mammalian cells are well known in the art.

Kits may be made using the cells of the present invention. They may comprise other components which are useful for performing assays. These may be, for example, particular assay reagents, microtiter plates, instructions for performing assays or for growing the cells. The reagents may be for growing the cells in vitro or for assaying the cells for proliferative index. Exemplary of such reagents are labeled amino acids or nucleotides.

In vitro expanded populations of $CD4^+CD25^+$ regulatory T cells are cells that have increased in cell number by at least 5-fold, 10-fold, 15-fold, 20-fold, 25-fold, 30-fold, 50-fold, 100-fold, 1000-fold, 10,000-fold or 100,000-fold. The manner of stimulating the cells to proliferate in vitro can lead to a particular subpopulation of cells having particular marker expression and function. Thus, for example, populations stimulated with 4-1BBL will express the 4-1BB receptor on their surface. These cells remain anergic even after expansion.

In vitro expanded populations of $CD4^+CD25^+$ regulatory T cells can be used for testing substances for their ability to stimulate proliferation of the cells. Substances which are able to stimulate the proliferation are candidate therapeutic agents for treating human auto-immune diseases, such as graft versus host disease, Hashimoto's thyroiditis, pernicious anemia, Addison's disease, diabetes, rheumatoid arthritis, systemic lupus erythematosus, dermatomyositis, Sjogren's syndrome, multiple sclerosis, myasthenia gravis, systemic sclerosis (scleroderma), Reiter's syndrome, and Grave's disease. Immune-mediated diseases in other mammals may also be treated according to the present invention. A common form of immune disease in dogs and cats, for example, is immune mediated hemolytic anemia. Other immune mediated diseases that can be treated in mammals other than humans include but are not limited to host versus graft disease, immune-mediated thryroiditis, Cobalamin deficiency, Addison's disease or hypoadrenocorticism, diabetes mellitus, Rheumatoid arthritis, immune-mediated arthropathies, including SLE, Dermatomyositis, Sjorgen's Syndrome, and immune-mediated keratoconjunctival sicca. Substances can be further checked using other types of assays or other animal model tests. These same diseases can be treated by administration of in vitro expanded populations of $CD4^+CD25^+$ regulatory T cells according to the invention. Similarly, these same diseases can be treated with soluble 4-1BBL-Fc, or other 4-1BBL constructs. Cells which are "painted" with 4-1BBL-Fc can also be delivered to a mammal in need thereof to stimulate in vivo proliferation of $CD4^+CD25^+$ regulatory T cells.

Suitable substances for testing for stimulatory activity are any natural or synthetic products, including products of libraries of compounds and peptides. The substances can be those previously known to have a biological activity or a therapeutic activity, or the substances can have non previously known activities. Libraries of compounds are available for testing commercially or can be made by the ordinary artisan.

Painted cells can have additional ligands painted on their surfaces. These include any ligands that stimulate $CD4^+CD25^+$ regulatory T cells directly or ligands that stimulate accessory cells which stimulate $CD4^+CD25^+$ regulatory T cells. Suitable ligands in addition to 4-1BBL include without limitation OX40L, ICOSL, anti-CD28 antibodies, CTLA-4, and anti-CD3 antibodies.

Although enhanced in vivo expansion of the 4-1BBL-Fc-treated $CD4^+CD25^+$ T cells is evident in our study, it is far less extensive than that demonstrated previously in animals immunized with either a soluble antigen or mature DC loaded with an antigen[12-14]. The sub-optimal amount of OVA antigen applied in our experiments may have attributed to the result. In addition, 4-1BB alone may be insufficient to bring about the full force of co-stimulation as in vivo immunizations did. In those latter experiments, host DC activated upon encountering a large dose of immunizing antigen, or donor DC activated prior to transfusion, are likely to express not one, but a spectrum of co-stimulators. As these co-stimulators may engage several receptors on the $CD4^+CD25^+$ T cells, such as 4-1BB, OX40, and CD28 and/or CTLA-4[18, 19], their combined effect could be greater than what 4-1BB alone could produce. It will be interesting to test whether multiple recombinant co-stimulators can indeed elicit stronger functional outputs from $CD4^+CD25^+$ T cells.

In vivo expansion of $CD4^+CD25^+$ T cells can be used for controlling harmful auto-immune and allo-immune reactions. Other means for expanding $CD4^+CD25^+$ T cells (other than using a co-stimlatory molecule) can be used in conjunction with 4-1BBL, such as antigen immunization[12, 13], infusion of antigen-presenting dendritic cells (DC)[14], and various other methods for ex vivo and in vivo expansion[9, 20-22].

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1

Materials and Methods

Mice, Peptide, and Cell Line

BALB/c and DO11.10 [BALB/c-TgN(DO11.10)10Loh] mice were purchased from the Jackson Laboratory (Bar Harbor, Me.). The animals were maintained in a pathogen-free facility and used in accordance with institutional guidelines for animal care. The $OVA_{323-339}$ antigen peptide was synthesized by Princeton Biomolecules (Langhorne, Pa.). The PRO-1Ad cell line was a gift from Jim Miller of the University of Chicago and maintained as previously described[23].

Antibodies

PE-conjugated hamster anti-mouse 4-1BB mAb (17B5), PE-conjugated rat anti-mouse 4-1BBL mAb (TKS-1), and isotype controls were purchased from eBioscience (San Diego, Calif.). Non-conjugated 4-1BB-blocking mAb (17B5) was also purchased from eBioscience and dialyzed in PBS before use. PE-conjugated goat anti-human $Fc_\gamma$ was purchased from The Jackson ImmunoResearch Laboratories (West Grove, Pa.). Rat anti-mouse CD3 mAb (TK3) was purchased from Serotec Ltd. (Oxford, UK). FITC-conjugated rat anti-mouse 4-1BB mAb (1AH2), FITC-conjugated rat anti-mouse CD4 mAb (GK1.5), APC-conjugated rat anti-mouse CD4 mAb (RM4-5), biotin-conjugated rat anti-mouse CD25 mAb (7D4), PE- or APC-conjugated streptavidin, rat anti-mouse CD16/CD32 mAb (2.4 G2), and various isotype-matched controls were purchased from BD Biosciences (San Jose, Calif.). PE-conjugated mouse anti-DO11.10 mAb (KJ1-26) was purchased from Caltag Laboratories (Burlingame, Calif.).

T Cell Purification

CD4+ T cells were prepared from the spleens or lymph nodes of BALB/c or DO11.10 mice and enriched via negative selection by magnetic cell sorting (Miltenyi Biotec, Auburn, Calif.), as per manufacturer's protocols. The cells were blocked with anti-mouse CD16/CD32 mAb, immunostained with FITC-conjugated anti-mouse CD4 mAb and biotin-conjugated anti-mouse CD25 mAb/PE-conjugated streptavidin, and then sorted by a FACSDiVa cell sorter (BD Biosciences). CD4+CD25+ and CD4+CD25− cells were separately collected; purity of the preparations was typically >98%. For some experiments, the CD4+CD25+ and CD4+CD25− cells were purified by magnetic cell sorting, using the CD4+CD25+ regulatory T cell isolation kit from Miltenyi Biotec, as per manufacturer's protocol. To obtain highly purified cells, the MS column step was repeated three times before the CD4+CD25+ cells were finally collected. The purity of such cell preparations were typically >98%, whereas the yield was reduced by about 40%.

Cell Painting

PRO-IAd artificial accessory cells were inactivated by incubation at 37° C. for 1 h with 100 μg/ml of mitomycin C (Sigma-Aldrich Corp., St. Louis, Mo.), at $2 \times 10^6$ cells/ml in DMEM/2% FCS. The cells were thoroughly washed and incubated at 37° C. for 30 min with palmitated protein A[24], at 30 μg/$10^6$ cells/ml in DMEM/0.1% BSA. The cells were washed and incubated at 4° C. for 30 min with $Fc_{\gamma1}$-derivatized mouse 4-1BBL (4-1BBL-Fc)[25] or $Fc_{\gamma1}$-derivatized human CD28 (CD28-Fc)[24], at 30 μg/$10^6$ cells/ml in DMEM/0.1% BSA. The cells were thoroughly washed and suspended in RPMI 1164/10% FCS/15 mM HEPES/50 μM β-ME (R10 medium).

Proliferation Assay $0.25\text{-}1 \times 10^5$ T cells (per well) were cultured in R10 medium in U-bottomed 96-well plates in duplicates or triplicates, along with $2.5\text{-}5 \times 10^4$ PRO-IAd cells (per well) painted with 4-1BBL-Fc or 4 μg of soluble 4-1BBL-Fc (per well). For Ab blocking, anti-4-1BB mAb (17B5) and isotype-matched control were each used at 5 μg per well. For assays involving the DO11.10 TCR transgenic T cells, the $OVA_{323\text{-}339}$ peptide was added to the wells at 0.1-100 μg/ml, in conjunction with the PRO-IAd cells. For assays involving BALB/c T cells, rat anti-mouse CD3 mAb (TK3) was used as a polyclonal mitogen. The mAb was diluted to 1-8 μg/ml in PBS and bound to U-bottomed 96-well plates (50 μl per well) at 37° C. for at least 6 h before the cells were plated. The cultures were pulsed at 48 h with $^3$H-thymidine (1 μCi per well) and harvested at 64 h with a Tomtec MACH III cell harvester (Hamden, Conn.). $^3$H-thymidine incorporation was analyzed with a MicroBeta liquid scintillation counter (Wallac Oy, Turku, Finland).

Adoptive Transfer

CD4+CD25+ T cells were purified from the spleens of DO11.10 mice as described earlier, washed three times in PBS, thoroughly re-suspended at $2.5 \times 10^6$ cells/ml in PBS, and then stained with CFSE (Molecular Probes, Eugene, Oreg.) at 1 μM for 5 min at room temperature. The reaction was terminated by adding FCS to 10%, followed by two washes with DMEM/10% FCS/50 μM β-ME. For co-stimulator treatment, CFSE-stained cells were re-suspended in DMEM/0.1% BSA/50 μM β-ME and incubated at 4° C. for 20 min with 4-1BBL-Fc or human IgG (30 μg protein/$1 \times 10^7$ cells/ml). The cells were washed twice in DMEM and injected into the hind leg footpads of two or more BALB/c mice ($2.5\text{-}5 \times 10^5$ cells in 30 μl of DMEM per footpad). 4-1BBL-Fc-treated cells were injected at the right footpads; human IgG (control Fc)-treated cells, left footpads. To prime the injected donor cells, 30 min prior to cell transfer, the $OVA_{323\text{-}339}$ peptide (0.08 μg in 30 μl of PBS per footpad) was injected into the right and left footpads of the recipient mice. The recipient mice were maintained in the dark for four days and then sacrificed. Cell suspensions were prepared from the right (4-1BBL-Fc-treated) and left (human IgG-treated) popliteal LNs; cells from each treatment group were pooled. The pooled cells were then immunostained for CD4 and the DO11.10 TCR with APC-conjugated anti-mouse CD4 mAb and PE-conjugated anti-DO11.10 mAb, respectively, in the presence of anti-mouse CD16/CD32 mAb as Fc blocker. Immediately before FACS analysis, the cells were additionally stained for DNA with 7-AAD (Molecular Probes, Eugene, Oreg.). Four-color FACS was performed on a FACSCalibur. The donor cells were gated as a DO11.10 TCR and CD4 double-positive population, and the viability (7-AAD negativity) and cell division (CFSE decrement) of this gated population were analyzed with the Cellquest software.

Co-Adoptive Transfer

CFSE-labeled DO11.10 CD4+CD25+ T cells prepared as described before were pre-mixed with antigen-pulsed and 4-1BBL-painted PRO-IAd cells and injected in the form of a cell mixture into the footpad of BALB/c mice. For preparation of the PRO-IAd cells for co-adoptive transfer, the cells were inactivated with mitomycin C as described before and incubated with the $OVA_{323\text{-}339}$ peptide (80 μM) at 37° C. for 1 h, at $10^7$ cells/ml in DMEM/0.1% BSA. Palmitated protein A was then added to the cells at 30 μg/ml and the incubation was continued for another 50 min at 37° C., followed by 10 min incubation at 45° C. The cells were washed and incubated at 4° C. for 20 min with 4-1BBL-Fc or, as control, human IgG, at 30 μg/$10^6$ cells/ml in DMEM/0.1% BSA. The cells were washed twice in DMEM and combined with the T cells at 1:1 ratio. Footpad injection (two or more mice per experiment) and FACS analysis were performed essentially as described before, with the mixed cells containing the human IgG-pained PRO-IAd cells injected ($0.5\text{-}1 \times 10^6$ total cells per foot) into the left footpads (control) and an equal number of mixed cells containing the 4-1BBL-painted PRO-IAd cells injected into the right footpads (test).

Suppression Assay

DO11.10 CD4+CD25+ or CD4+CD25− T cells were stimulated to proliferation with mitomycin C-inactivated, 4-1BBL-Fc-painted PRO-IAd cells and $OVA_{323\text{-}339}$ (10 μg/ml) in U-bottomed 96-well plates and R10 medium. The cells were harvested three days later and thoroughly washed in R10 medium. Live cells (T cells) were counted and re-seeded as suppressor ($0.025 \times 10^6$ cells/well) in U-bottomed 96-well plates in R10 medium, together with freshly isolated DO11.10 CD4+CD25− T cells as responder ($0.05 \times 10^6$ cells/well), DO11.10 accessory cells as stimulator ($0.05 \times 10^6$ cells/well), and $OVA_{323\text{-}339}$ (0.1 μg/ml). The accessory cells were obtained from bulk spleen cells depleted of CD4+ and CD8+ cells by magnetic cell sorting (Miltenyi Biotec) and chemically inactivated with mitomycin C before use. The proliferation of the responder T cells was determined by the $^3$H-thymidine incorporation method described before.

4-1BBL-Fc Construct

An expression construct for 4-1BBL-Fc was assembled via splicing PCR, in several steps. A coding sequence for the extracellular domain of murine 4-1BBL was synthesized using primers F (5'-GTGCCACGCCTCGAGCGCAC-CGAGCCTCGGCC-3'; SEQ ID NO: 5) and G (5'-T ACTGGA TCCTCA TTCCCA TGGGTTGT CGGG-3';

SEQ ID NO: 6), along with a plasmid containing murine 4-1BBL cDNA (a generous gift from Dr. Lieping Chen) as template. The resulting PCR product was digested with BamHI and XhoI, and subcloned into the corresponding sites of pBluescript, to generate pm4-1BBL/BT. In turn, the murine 4-1BBL extracellular domain sequence was mobilized from pm4-1BBL BT IBBL BT with NotI, filled-in with Klenow, digested with XhoI, and subcloned into a derivative of pEE14 that contains human $Fc_{\gamma 1}$ sequence upstream of the corresponding site, to generate pm4-1BBL-Fc/EE14.

The murine TNFSF9 gene sequence segment contained in the 4-1BBL-Fc construct is:

(SEQ ID NO: 7)
CGCACCGAGCCTCGGCCAGCGCTCACAATCACCACCTCGCCCAACCTGGG

TACCCGAGAGAATAATGCAGACCAGGTCACCCCTGTTTCCCACATTGGCT

GCCCCAACACTACACAACAGGGCTCTCCTGTGTTCGCCAAGGTACTGGCT

AAAAACCAAGCATCGTTGTGCAATACAACTCTGAACTGGCACAGCCAAGA

TGGAGCTGGGAGCTCATACCTATCTCAAGGTCTGAGGTACGAAGAAGACA

AAAAGGAGTTGGTGGTAGACAGTCCCGGGCTCTACTACGTATTTTTGGAA

CTGAAGCTCAGTCCAACATTCACAAACACAGGCCACAAGGTGCAGGGCTG

GGTCTCTCTTGTTTTGCAAGCAAAGCCTCAGGTAGATGACTTTGACAACT

TGGCCCTGACAGTGGAACTGTTCCCTTGCTCCATGGAGAACAAGTTAGTG

GACCGTTCCTGGAGTCAACTGTTGCTCCTGAAGGCTGGCCACCGCCTCAG

TGTGGGTCTGAGGGCTTATCTGCATGGAGCCCAGGATGCATACAGAGACT

GGGAGCTGTCTTATCCCAACACCACCAGCTTTGGACTCTTTCTTGTGAAA

CCCGACAACCCATGGGAA

The murine TNFSF9 protein sequence segment contained in the 4-1BBL-Fc construct is:

(SEQ ID NO: 8)
RTEPRPALTITTSPNLGTRENNADQVTPVSHIGCPNTTQQGSPVFAKLLA

KNQASLCNTTLNWHSQDGAGSSYLSQGLRYEEDKKELVVDSPGLYYVFLE

LKLSPTFTNTGHKVQGWVSLVLQAKPQVDDFDNLALTVELFPCSMENKLV

DRSWSQLLLLKAGHRLSVGLRAYLHGAQDAYRDWELSYPNTTSFGLFLVK

PDNPWE

Example 2

Signaling of 4 1BB Augmented the Proliferation of CD4$^+$CD25$^+$ T Cells

Previously, Gavin et al.[18] and McHugh et al.[19] detected constitutive expression of the 4-1BB gene in mouse CD4+ CD25+ T cells using DNA microarray. To confirm the actual presence of the 4-1BB protein on the cell surface, we isolated spleen cells from normal BALB/c mice and their congenics carrying a rearranged TCR transgene (DO11.10), and immunostained the cells with hamster anti-mouse 4-1BB antibody (17B5), together with antibodies specific for CD4 and CD25. Using multi-color flow cytometry, we were able to identify and gate on CD4+CD25+ and CD4+CD25− T cells and examine the 4-1BB-specific stains simultaneously in both subsets (FIG. 1A). The CD4+CD25− subset served as an internal control, since naïve CD4+CD25− T cells are known to express little 4-1BB[16]. Indeed, in the freshly isolated spleen cells of BALB/c or DO11.10 origins, 4-1BB was detected only in the CD4+CD25+ subset, but not in the CD4+ CD25− subset (FIGS. 1B & 1C). However, the 4-1BB stain in the CD4+CD25+ subset was rather weak, suggesting a low-level presence of the 4-1BB protein on the cell surface. This observation was confirmed with the use of a second anti-4-1BB mAb (1AH2) of different species origin (rat) (data not shown), and with the use of a ligand of 4-1BB, 4-1BBL-Fc[25], as the 4-1BB-specific staining reagent (FIG. 1B).

To investigate whether the level of 4-1BB expression in the CD4+CD25+ T cells changes after T cell activation, splenic CD4+CD25+ T cells were isolated and stimulated for two days in culture with anti-CD3 mAb and IL-2. The cells so activated were again stained with anti-4-1BB mAb. Flow cytometric analysis of these cells detected considerably stronger staining than what had been detected in the freshly isolated same cells (FIG. 1D), suggesting that the presence of 4-1BB on the cell surface is up-regulated after cell activation.

Figure 2A:
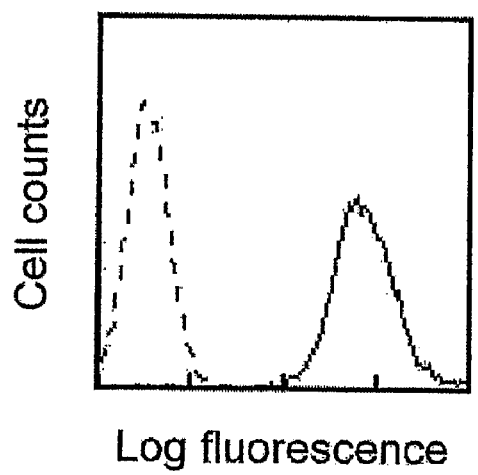
FIGS. 2A and 2B show that signaling of 4-1BB augments CD4+CD25+ T cell proliferation.
Figure 2B:
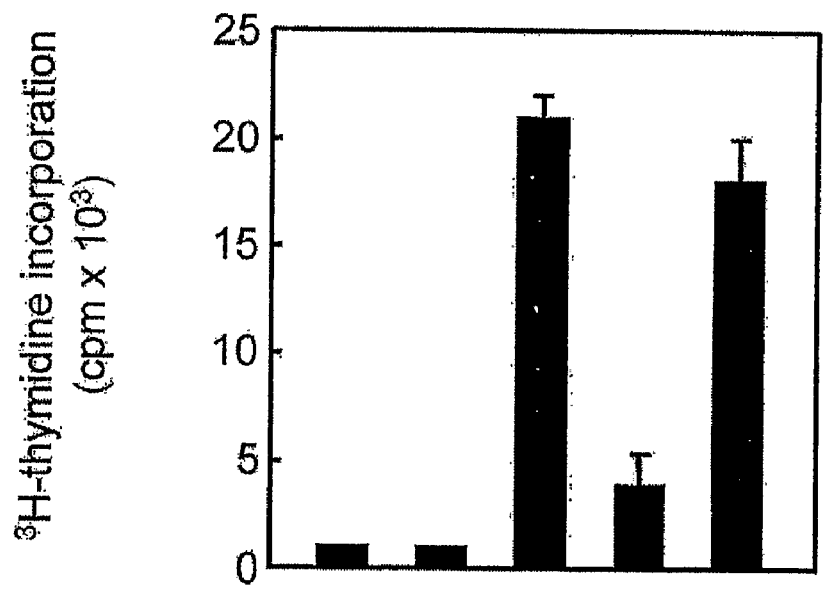

To determine whether the low-level presence of 4-1BB on CD4$^+$CD25$^+$ T cells is functionally significant, we next probed the cells with a ligand of 4-1BB, 4-1BBL-Fc[25]. To that end, 4-1BBL-Fc was painted onto an artificial accessory cell line, PRO-IAd (FIG. 2A). Splenic CD4$^+$CD25$^+$ T cells isolated from BALB/c mice were stimulated in culture with plated-bound anti-CD3 mAb, in combination with the PRO-IAd IAd cells. As expected, the CD4$^+$CD25$^+$ T cells displayed a typical anergic phenotype and proliferated poorly in response to anti-CD3 stimulation alone (FIG. 2B). However, they proliferated actively when co-stimulated by PRO-IAd cells painted with 4-1BBL-Fc, but not with a control Fc protein (CD28-Fc), indicating that the cells were sensitive to 4-1BBL co-stimulation. The activity was blocked by anti-4-1BB mAb, confirming that it was specifically mediated by the 4-1BB receptor. These results establish that the low-level expression of 4-1BB on CD4$^+$CD25$^+$ T cells is sufficient to render the cells sensitive to 4-1BBL co-stimulation, and that such co-stimulation can potently drive the cells to proliferation. Additional experiments with CD4$^+$CD25$^+$ T cells isolated from the lymph nodes showed that 4-1BBL-Fc could also co-stimulate these cells to proliferate, as expected (data not shown).

Figure 7:
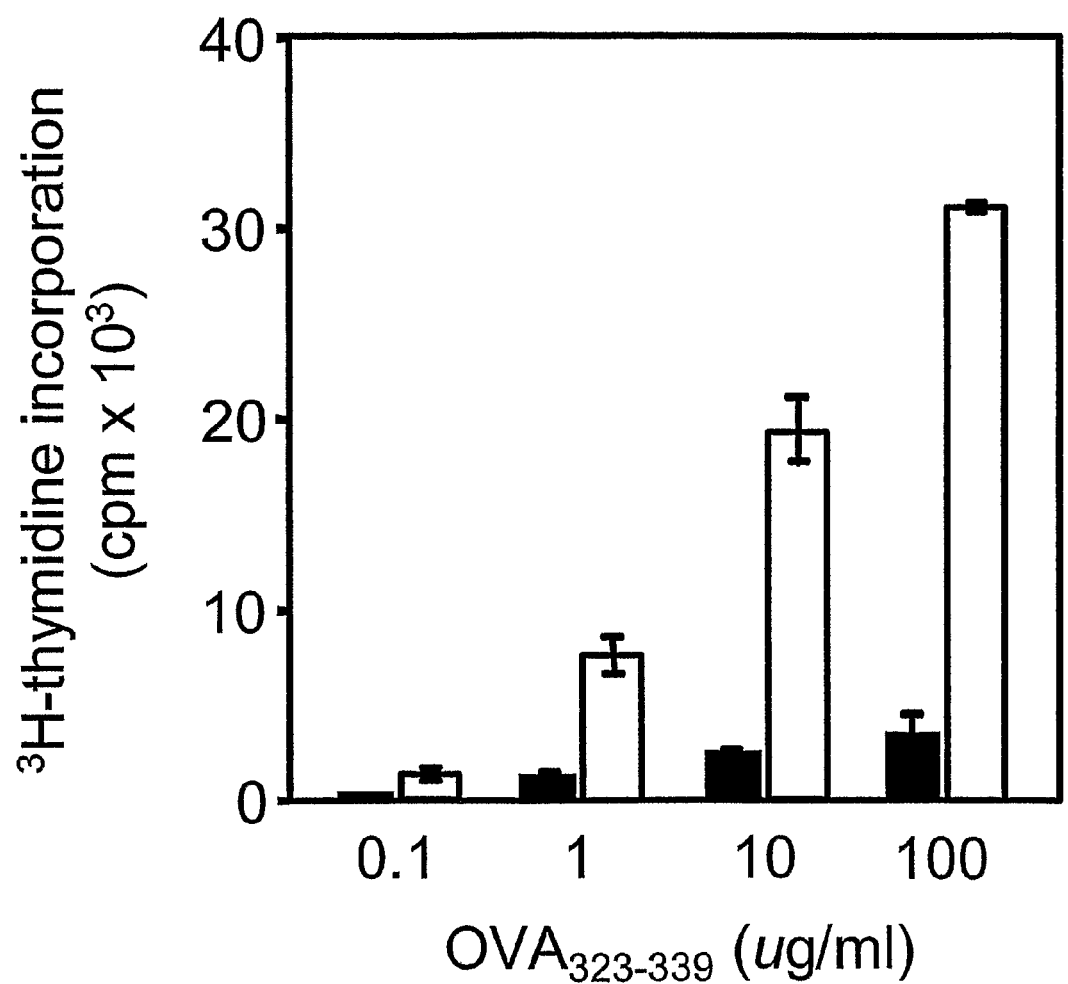
FIG. 7 shows that 4-1BB co-stimulation augmented antigen-specific proliferation of DO11.10 CD4$^+$CD25$^+$ T cells. DO11.10 splenic CD4$^+$CD25$^+$ T cells were stimulated with indicated concentrations of the OVA$_{323-339}$ peptide antigen, presented by the PRO-IAd artificial APC that were generated by painting with 4-1BBL-Fc (open bar) or human IgG as control Fc protein (filled bar). Cell proliferation was determined as described in FIG. 2. Data are representative of two independent experiments.

To probe the effect of 4-1BB engagement on antigen-specific proliferation, the PRO-IAd cells, which neo-express the MHC II molecules I-A$^d$ molecules on the cell surface[23], were further tested as antigen presenting cells (APC) for CD4+ CD25+ T cells bearing the DO11.10 transgenic TCR. When painted with 4-1BBL-Fc and loaded with the cognate OVA323-339 peptide antigen, the artificial APC vigorously stimulated the proliferation of the antigen-specific CD4+ CD25+ T cells over a range of antigen doses (FIG. 7). In contrast, the same APC showed only marginal stimulatory activity when painted with a control Fc-containing protein (human IgG). This result confirms that 4-1BB co-stimulation can promote antigen-specific proliferation of CD4+CD25+ T cells.

4-1BB binds 4-1BB ligand with high affinity[26, 27]. Although both exist predominantly as membrane proteins, the high affinity interaction between the two allows the receptor to be triggered by soluble forms of 4-1BB ligand as well, as has been observed in conventional T cells[28]. To determine whether this may also be the case for CD4$^+$CD25$^+$ regulatory T cells, we applied soluble 4-1BBL-Fc directly to cell proliferation assays, without invoking artificial accessory cells to present the ligand. The proliferation of CD4$^+$CD25$^+$ T cells over a range of anti-CD3 stimulation was consistently augmented by the addition of soluble 4-1BBL-Fc (FIG. 3), suggesting that the 4-1BB receptor on these cells can be triggered directly by a soluble ligand. This finding enabled us to directly "coat" CD4$^+$CD25$^+$ T cells with soluble 4-1BBL-Fc for in vivo studies.

To determine whether 4-1BB could co-stimulate antigen-specific proliferation of CD4$^+$CD25$^+$ T cells in vivo, TCR transgenic CD4$^+$CD25$^+$ T cells were isolated from the spleens of DO11.10 mice and labeled with CFSE to allow subsequent analysis of cell division by FACS[29]. The labeled cells were incubated at 4° C. with 4-1BBL-Fc to allow binding of the protein to the 4-1BB receptor on the cell surface; unbound ligand was subsequently removed by washing. The treated cells were adoptively transferred via footpad injection into syngeneic BALB/c mice. As control, an equal number of mock-treated T cells (incubated with human IgG as control Fc proteins) were injected into the contralateral footpads of the same animals. To provide specific antigen stimulation to the donor cells, the recipient mice were also injected at the footpads with OVA$_{323-339}$, a cognate antigen peptide recognized by the DO11.10 TCR, 30 min prior to cell transfusion. Four days after priming, draining LNs (popliteal) were isolated from the recipient mice and pooled from each group separately (test or control). Total cellular content of each group of pooled LNs was recovered and analyzed in its entirety by FACS to assure that all LN cells were accounted for.

Preliminary experiments established that the proliferation of donor CD4$^+$CD25$^+$ T cells in recipient animals is antigen dose-dependent (data not shown), consistent with previous reports by others[12-14]. In our hand, donor cell proliferation could not be detected at the antigen dose below 0.03 μg per footpad. Proliferation became obvious as the antigen dose increased; at 0.4 μg per footpad, nearly all the donor cells proliferated. To limit the antigen dose to a sub-optimal level where the effect of co-stimulation would be most obvious, recipient animals were injected with only 0.08 μg of peptide per footpad.

Figures 4A, 4B, 4C, 4D:
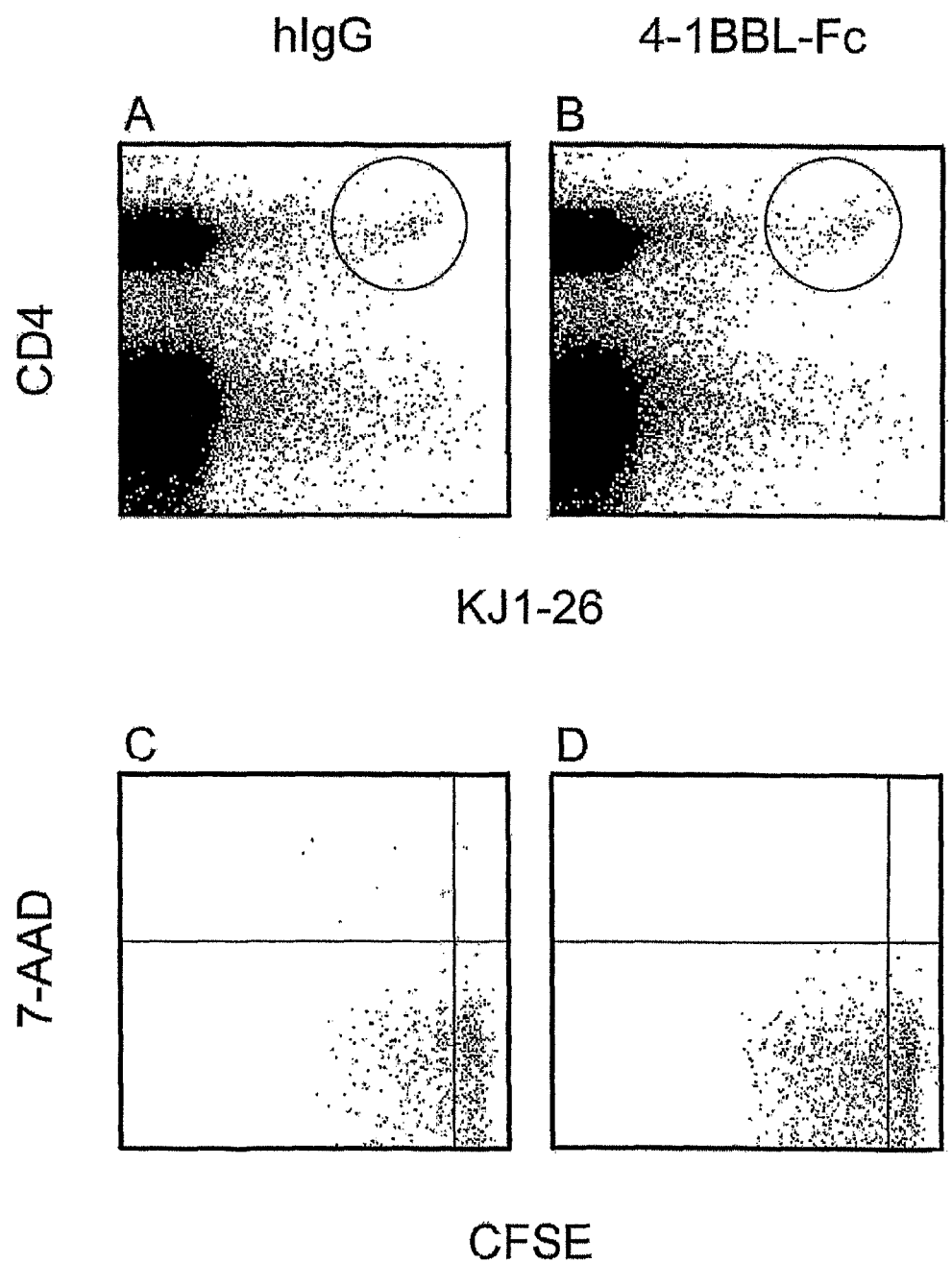
FIGS. 4A-4D demonstrate that 4-1BB ligand-coated CD4$^+$ CD25$^+$ T cells exhibited enhanced proliferative activity in vivo. CFSE-labeled DO11.10 TCR transgenic CD4$^+$CD25$^+$ T cells (99% pure), treated either with a human IgG control Fc protein (FIGS. 4A & 4C) or with 4-1BBL-Fc (FIGS. 4B & 4D), were injected contralaterally into the left and right footpad, respectively, of syngeneic BALB/c mice (Materials and Methods). At day 4, cells were recovered from the draining (popliteal) LNs and stained with APC-conjugated anti-CD4 mAb (RM4-5), PE-conjugated anti-DO11.10 mAb (KJ1-26), and 7-AAD. The cells were analyzed by four-color flow cytometry.

4-1BBL-Fc augmented in vivo expansion of the donor cell population under this antigen-limiting condition. Four-color FACS showed that the counts of donor cells, identifiable by their CD4+KJ1-26+ (DO11.10 TCR-specific) status, were increased by an average (three experiments) of 2-fold in the test group relative to that in the control group (FIGS. 4A & 4B). CFSE analysis further showed that in both groups the donor cell population was divided into two major fractions—the dividing-cell fraction (with incrementally-decreased CFSE stain, lower left quadrant) and non-dividing-cell fraction (with highest CFSE stain, lower right quadrant) (FIGS. 4C & 4D). While the counts of non-dividing cells were relatively even across the test and control groups, that of dividing cells were increased by an average (three experiments) of 2.5 fold in the test group. Taken together, the analyses indicated that the donor cell population in the test group was expanded primarily by augmented cell proliferation.

Figures 8A, 8B, 8C, 8D:
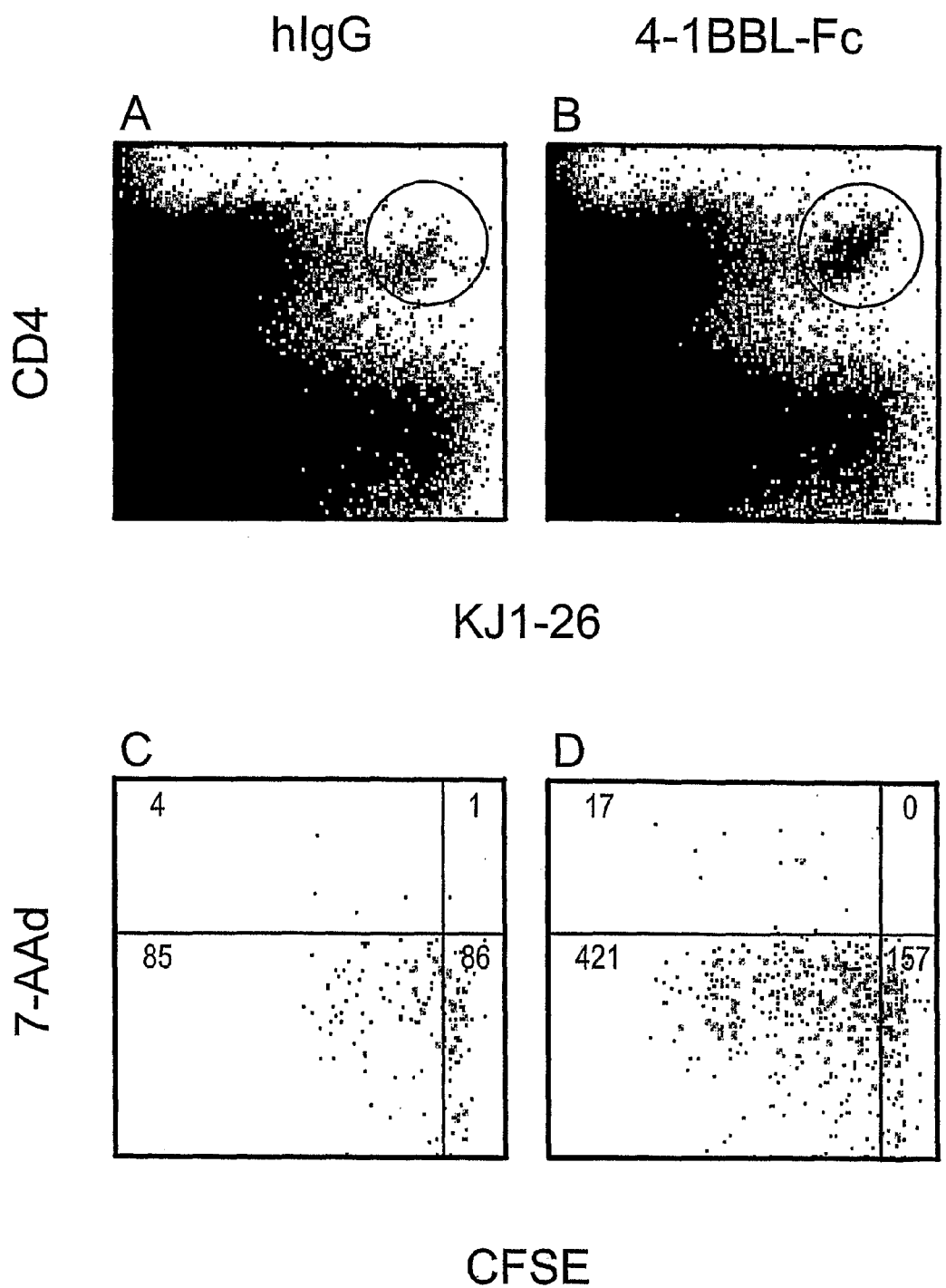
FIGS. 8A-8D show that CD4$^+$CD25$^+$ T cells proliferated more vigorously in vivo in response to artificial APC presenting 4-1BBL-Fc. CFSE-labeled DO11.10 TCR transgenic CD4$^+$CD25$^+$ T cells (98% pure) were pre-mixed with PRO-IAd cells painted with human IgG (FIGS. 8A & 8C) or the same PRO-IAd cells painted with 4-1BBL-Fc (FIGS. 8B & 8D), and the two different cell mixtures were injected counter-laterally into the left and right footpads, respectively, of BALB/c mice. At day 4, donor cell were recovered and analyzed by four-color flow cytometry. Similarly, donor cell population (CD4 and KJ1-26 double positive, circled) was gated on (FIGS. 8A & 8B) and proliferation (decrement of CFSE fluorescence) and death (7-AAD positive stain) of the gated cells were analyzed by quadrant plots (FIGS. 8C & 8D). Cell count is indicated for each quadrant. Data are representative of four independent experiments. Compared to the control (FIG. 8C), the increase in the counts of proliferating cells (lower left quadrant) caused by 4-1BBL-Fc-painted APC (FIG. 8D) is statistically significant by one-tailed Student t test (p<0.025).

To further demonstrate such augmented proliferation in a setting more closely simulating the physiological priming of T cells, a co-adoptive transfer experiment was performed where the donor T cells were transfused together with PRO-IAd cells as artificial APC. The PRO-IAd cells used were pre-loaded with OVA323-339 and painted with 4-1BBL-Fc. The resulting artificial APC were capable of stimulating the proliferation of DO11.10 CD4+CD25+ T cells as demonstrated earlier in vitro (FIG. 7). In parallel, the same PRO-IAd cells loaded with antigen but painted with human IgG were used as control. Footpad injection and FACS analysis were performed essentially as described before, except the donor T cells were pre-formulated with the artificial APC (1:1) and administered as a cell mixture. The result showed that the donor T cells co-transferred with the 4-1BBL-Fc-painted APC proliferated more vigorously as compared to those co-transferred with the control APC (FIG. 8). Again, on average (four experiments), there was a 4-fold increase in the counts of proliferating donor T cells that was directly attributable to the presence of 4-1BBL-Fc on APC. This result agrees well with the earlier result obtained from the 4-1BBL-Fc-coated donor T cells Example 3

4-1BB Co-Stimulation did not Involve IL-2 Production

Figure 5:
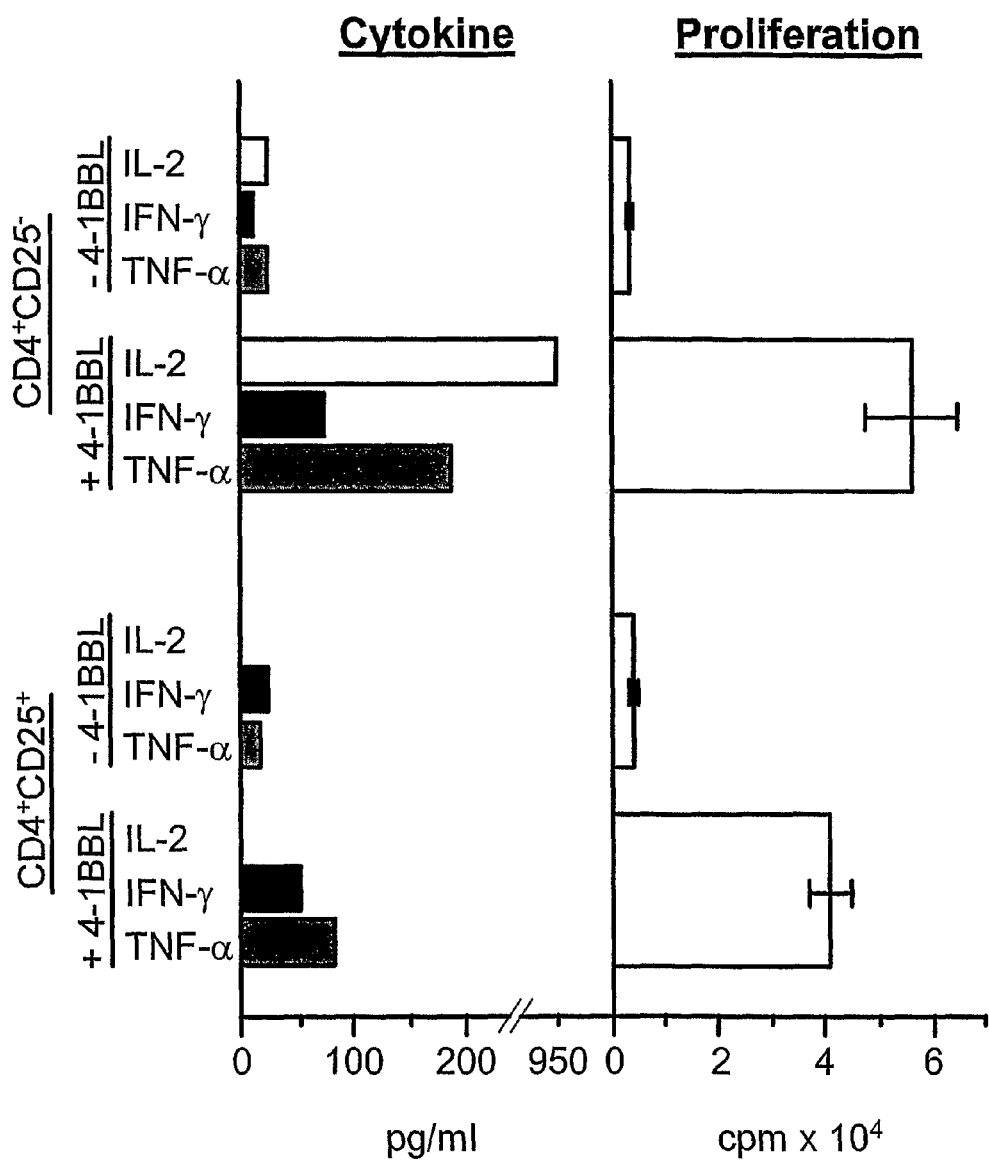
FIG. 5 demonstrates that 4 1BB co-stimulated, proliferating CD4$^+$CD25$^+$ T cells do not produce IL-2. CD4+CD25+ or CD4+CD25- T cells (in 200 μl) were stimulated (in duplicate) with plate-bound anti-CD3 (bounded at 8 μg/ml for CD4+CD25+ cells and 4 μg/ml for CD4+CD25- cells) and soluble 4-1BBL-Fc (4 μg per well). At 48 h, 50 μl of conditioned medium was taken from each of the duplicate wells and combined, and cytokine content in the medium was analyzed with Cytometric Bead Array (BD Biosciences). In parallel, the remaining cultures were pulsed with 3H-thymidine (1 μCi per well), and the proliferation of the cytokine-producing T cells was assessed as described in FIGS. 2A and 2B. Data are representative of two independent experiments.

Activated T cells are known to secrete IL-2 that in turn initiates an autocrine loop for the continued expansion and survival of the proliferating population. However, this has not been the case for the CD4$^+$CD25$^+$ regulatory T cell subset expanded in culture, including those expanded under anti-CD28 co-stimulation[21, 30]. To determine whether 4-1BB co-stimulation in particular can result in IL-2 secretion, we stimulated the CD4$^+$CD25$^+$ T cells with anti-CD3 mAb and soluble 4-1BBL-Fc. 48 h after stimulation, a small portion of conditioned medium was taken from the culture and analyzed for IL-2, together with a penal of other cytokines (IL-4, IL-5, INF-γ, and TNF-α). To directly correlate cytokine secretion with cell proliferation, the rest of the same culture was also pulsed with $^3$H-thymidine and assayed for proliferation. No IL-2 was detected in proliferating CD4$^+$CD25$^+$ T cell cultures (FIG. 5). In contrast, IL-2 secretion was evident in parallel CD4$^+$CD25$^-$ T cell cultures that were stimulated to proliferation at a similar level. Like CD4$^+$CD25$^-$ T cells, however, CD4$^+$CD25$^+$ T cells did secrete increased amounts of IFN-γ and TNF-α during proliferation, albeit at considerably lower levels than that by CD4$^+$CD25$^-$ T cells. IL-4 and IL-5 were present only at marginal levels in both CD4$^+$CD25$^+$ and CD4$^+$CD25$^-$ T cell cultures and were not significantly increased upon proliferation (data not shown). These results suggest that, like anti-CD28 co-stimulation, the mechanism of 4-1BB co-stimulation in the context of CD4$^+$CD25$^+$ T cells may not involve IL-2 production.

Example 4

4-1BB-Expanded CD4$^+$CD25$^+$ T Cells Remained Suppressive

The CD4+CD25+ regulatory T cells are known to be able to suppress the proliferation of conventional T cells, which can be demonstrated by the well-established co-culture assay[31]. Such activity is generally limited toward weakly, but not strongly, stimulated T cells[31-34], with physiological implication that it might function primarily to raise the threshold of autoimmune reactions[33]. Having established the augmenting effect of 4-1BB co-stimulation on cell proliferation, we sought to determine whether the CD4+CD25+ T cells remained suppressive after proliferation.

Figure 3:
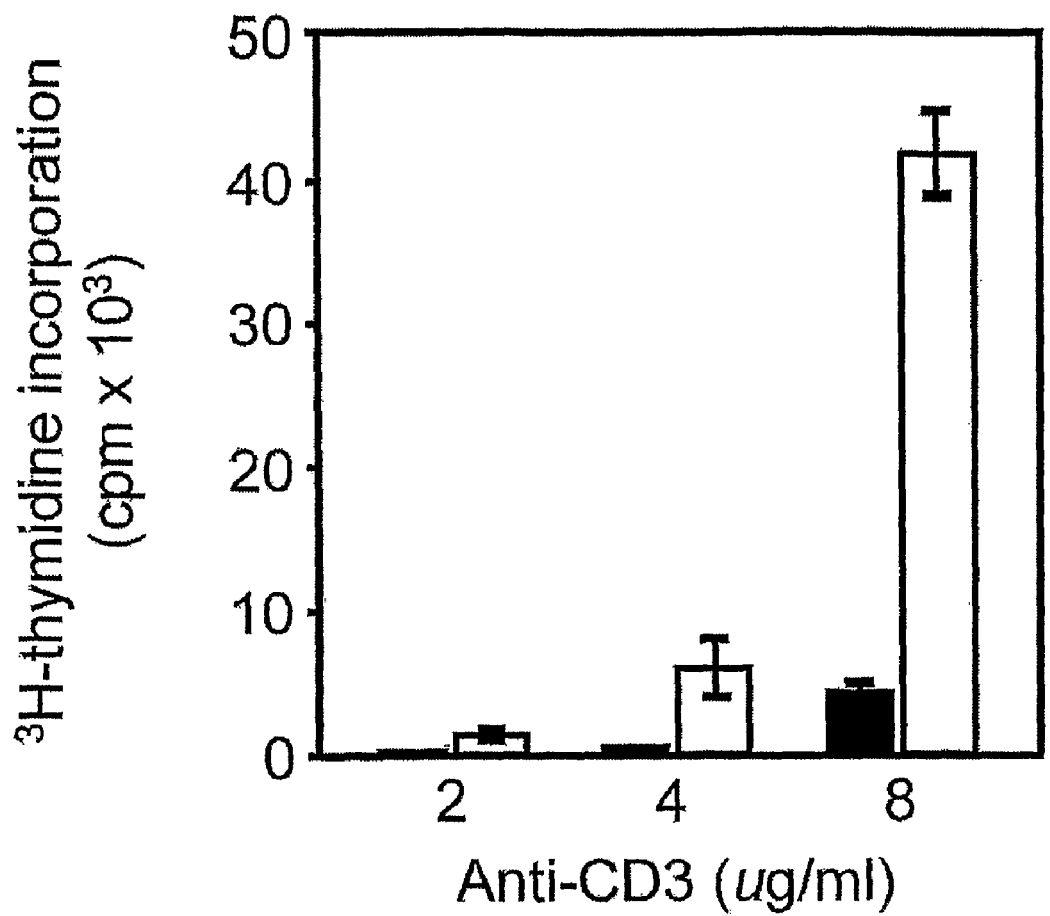
FIG. 3 demonstrates that soluble 4-1BB ligand co-stimulates CD4+CD25+ T cell proliferation. CD4+CD25+ T cells were stimulated with indicated concentrations of plate-bound anti-CD3 mAb, either alone (filled bar) or in combination with 4 μg of soluble 4-1BBL-Fc (open bar). Cell proliferation was determined as described in FIGS. 2A and 2B. Data are representative of three independent experiments.
Figure 6:
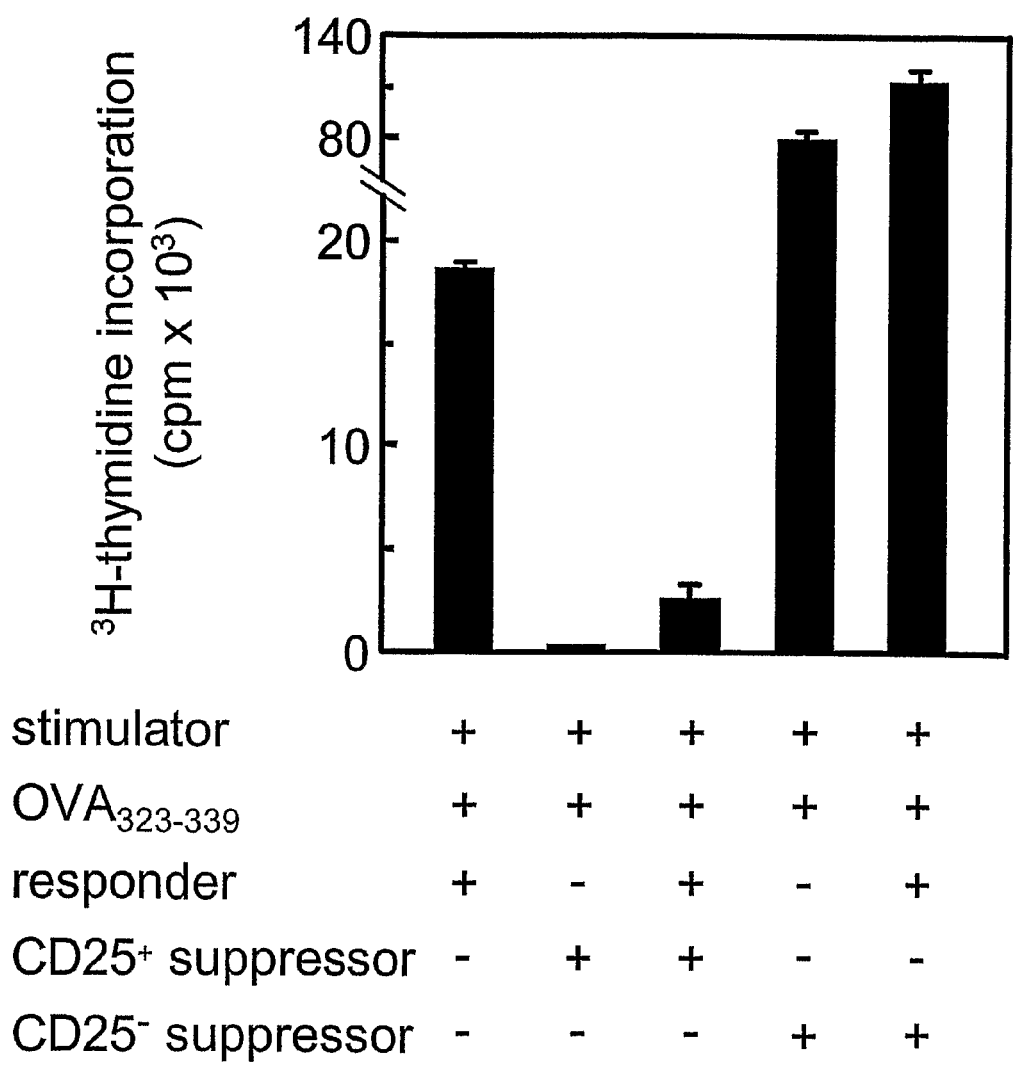
FIG. 6 demonstrates that 4-1BB-co-stimulated CD4$^+$ CD25$^+$ T cells remained suppressive. DO11.10 CD4$^+$CD25$^+$ or CD4$^+$CD25$^-$ T cells that had proliferated under 4-1BB co-stimulation for three days were harvested and tested as suppressor in co-culture, together with freshly isolated DO11.10 CD4$^+$CD25$^-$ T cells as responder, mitomycin C-treated DO11.10 spleen cells as stimulator, and the OVA$_{323-339}$ antigen peptide (0.1 μg/ml). The proliferation of the responder was determined by the $^3$H-thymidine incorporation method described in the description of FIG. 2. Data are representative of two independent experiments.

To that end, DO11.10 CD4+CD25+ T cells were first co-stimulated to proliferation with 4-1BBL-Fc-painted PRO-IAd cells and a high dose of OVA323-339 (10 μg/ml; FIG. 3). Three days later, the proliferating cells were harvested and their suppressive activity was subsequently assessed by the co-culture assay against DO11.10 CD4+CD25− T cells, in the presence of spleen-derived accessory cells and a low dose of OVA323-339 (0.1 μg/ml). As depicted in FIG. 6, the CD4+CD25+ T cells, which ceased to proliferate under this latter condition, were able to inhibit the proliferation of the CD4+CD25− T cells, indicating that the CD4+CD25+ T cells remained suppressive after proliferating under 4-1BB co-stimulation. In contrast, DO11.10 CD4+CD25− T cells pre-expanded identically in the same experiment did not exhibit such suppressive activity, suggesting that 4-1BB co-stimulation could not confer the suppressive activity to conventional T cells.

REFERENCES

1. Sakaguchi, S. et al. Immunologic tolerance maintained by CD25+ CD4+ regulatory T cells: their common role in controlling autoimmunity, tumor immunity, and transplantation tolerance. *Immunol Rev* 182, 18-32. (2001).
2. Shevach, E. M. CD4+CD25+ suppressor T cells: more questions than answers. *Nat Rev Immunol* 2, 389-400. (2002).
3. Curotto de Lafaille, M. A. & Lafaille, J. J. CD4(+) regulatory T cells in autoimmunity and allergy. *Curr Opin Immunol* 14, 771-778. (2002).
4. Takahashi, T. et al. Immunologic self-tolerance maintained by CD25+CD4+ naturally anergic and suppressive T cells: induction of autoimmune disease by breaking their anergic/suppressive state. *Int Immunol* 10, 1969-1980. (1998).
5. Salomon, B. et al. B7/CD28 costimulation is essential for the homeostasis of the CD4+CD25+ immunoregulatory T cells that control autoimmune diabetes. *Immunity* 12, 431-440. (2000).
6. Shimizu, J., Yamazaki, S. & Sakaguchi, S. Induction of tumor immunity by removing CD25+CD4+ T cells: a common basis between tumor immunity and autoimmunity. *J Immunol* 163, 5211-5218. (1999).
7. Sutmuller, R. P. et al. Synergism of cytotoxic T lymphocyte-associated antigen 4 blockade and depletion of CD25 (+) regulatory T cells in antitumor therapy reveals alternative pathways for suppression of autoreactive cytotoxic T lymphocyte responses. *J Exp Med* 194, 823-832. (2001).
8. van Maurik, A., Herber, M., Wood, K. J. & Jones, N. D. Cutting edge: CD4+CD25+ alloantigen-specific immunoregulatory cells that can prevent CD8+ T cell-mediated graft rejection: implications for anti-CD154 immunotherapy. *J Immunol* 169, 5401-5404. (2002).
9. Taylor, P. A., Lees, C. J. & Blazar, B. R. The infusion of ex vivo activated and expanded CD4(+)CD25(+) immune regulatory cells inhibits graft-versus-host disease lethality. *Blood* 99, 3493-3499. (2002).
10. Belkaid, Y., Piccirillo, C. A., Mendez, S., Shevach, E. M. & Sacks, D. L. CD4+CD25+ regulatory T cells control Leishmania major persistence and immunity. *Nature* 420, 502-507. (2002).
11. Kullberg, M. C. et al. Bacteria-triggered CD4(+) T regulatory cells suppress Helicobacter hepaticus-induced colitis. *J Exp Med* 196, 505-515. (2002).
12. Walker, L. S., Chodos, A., Eggena, M., Dooms, H. & Abbas, A. K. Antigen-dependent proliferation of CD4+ CD25+ regulatory T cells in vivo. *J Exp Med* 198, 249-258. (2003).
13. Klein, L., Khazaie, K. & von Boehmer, H. In vivo dynamics of antigen-specific regulatory T cells not predicted from behavior in vitro. *Proc Natl Acad Sci USA* 100, 8886-8891. (2003).
14. Yamazaki, S. et al. Direct expansion of functional CD25+ CD4+ regulatory T cells by antigen-processing dendritic cells. *J Exp Med* 198, 235-247. (2003).
15. Akbari, O. et al. Antigen-specific regulatory T cells develop via the ICOS-ICOS-ligand pathway and inhibit allergen-induced airway hyperreactivity. *Nat Med* 8, 1024-1032. (2002).
16. Kwon, B., Lee, H. W. & Kwon, B. S. New insights into the role of 4-1BB in immune responses: beyond CD8+ T cells. *Trends Immunol* 23, 378-380. (2002).
17. Linsley, P. S. et al. Human B7-1 (CD80) and B7-2 (CD86) bind with similar avidities but distinct kinetics to CD28 and CTLA-4 receptors. *Immunity* 1, 793-801. (1994).
18. Gavin, M. A., Clarke, S. R., Negrou, E., Gallegos, A. & Rudensky, A. Homeostasis and anergy of CD4(+)CD25(+) suppressor T cells in vivo. *Nat Immunol* 3, 33-41. (2002).
19. McHugh, R. S. et al. CD4(+)CD25(+) immunoregulatory T cells: gene expression analysis reveals a functional role for the glucocorticoid-induced TNF receptor. *Immunity* 16, 311-323. (2002).
20. Levings, M. K., Sangregorio, R. & Roncarolo, M. G. Human cd25(+)cd4(+) t regulatory cells suppress naive and memory T cell proliferation and can be expanded in vitro without loss of function. *J Exp Med* 193, 1295-1302. (2001).
21. Lin, C. H. & Hunig, T. Efficient expansion of regulatory T cells in vitro and in vivo with a CD28 superagonist. *Eur J Immunol* 33, 626-638. (2003).
22. Jiang, S., Camara, N., Lombardi, G. & Lechler, R. I. Induction of allopeptide-specific human CD4+CD25+ regulatory T cells ex vivo. *Blood* 102, 2180-2186. (2003).
23. Zuckerman, L. A., Sant, A. J. & Miller, J. Identification of a unique costimulatory activity for murine T helper 1 T cell clones. *J Immunol* 154, 4503-4512. (1995).
24. Chen, A., Zheng, G. & Tykocinski, M. L. Hierarchical costimulator thresholds for distinct immune responses: application of a novel two-step Fc fusion protein transfer method. *J Immunol* 164, 705-711. (2000).
25. Zheng, G. et al. Induction of antitumor immunity via intratumoral tetra-costimulator protein transfer. *Cancer Res* 61, 8127-8134. (2001).
26. Zhou, Z. et al. Characterization of human homologue of 4-1BB and its ligand. *Immunol Lett* 45, 67-73. (1995).
27. Pollok, K. E. et al. 4-1BB T-cell antigen binds to mature B cells and macrophages, and costimulates anti-mu-primed splenic B cells. *Eur J Immunol* 24, 367-374. (1994).
28. Salih, H. R. et al. Soluble CD137 (4-1BB) ligand is released following leukocyte activation and is found in sera of patients with hematological malignancies. *J Immunol* 167, 4059-4066. (2001).
29. Wells, A. D., Gudmundsdottir, H. & Turka, L. A. Following the fate of individual T cells throughout activation and clonal expansion. Signals from T cell receptor and CD28 differentially regulate the induction and duration of a proliferative response. *J Clin Invest* 100, 3173-3183. (1997).
30. Dieckmann, D., Plottner, H., Berchtold, S., Berger, T. & Schuler, G. Ex vivo isolation and characterization of CD4 (+)CD25(+) T cells with regulatory properties from human blood. *J Exp Med* 193, 1303-1310. (2001).
31. Thornton, A. M. & Shevach, E. M. CD4+CD25+ immunoregulatory T cells suppress polyclonal T cell activation in vitro by inhibiting interleukin 2 production. *J Exp Med* 188, 287-296. (1998).
32. Baecher-Allan, C., Brown, J. A., Freeman, G. J. & Hafler, D. A. CD4+CD25high regulatory cells in human peripheral blood. *J Immunol* 167, 1245-1253. (2001).
33. Baecher-Allan, C., Viglietta, V. & Hafler, D. A. Inhibition of human CD4(+)CD25(+high) regulatory T cell function. *J Immunol* 169, 6210-6217. (2002).
34. George, T. C., Bilsborough, J., Viney, J. L. & Norruent, A. M. High antigen dose and activated dendritic cells enable Th cells to escape regulatory T cell-mediated suppression in vitro. *Eur J Immunol* 33, 502-511. (2003).

The disclosure of each reference cited is expressly incorporated herein.

We claim:

1. A method of stimulating the proliferation of CD4+ CD25+ regulatory T cells in a diabetic mammal, comprising:
   administering an effective amount of soluble 4-1BBL to a diabetic mammal in need of immune suppression or immune toleration, whereby proliferation of CD4+ CD25+ regulatory T cells is stimulated; and
   immunizing the mammal with an antigen.

2. A method of stimulating the proliferation of CD4+ CD25+ regulatory T cells in a diabetic mammal, comprising:
   administering an effective amount of soluble 4-1BBL to a diabetic mammal in need of immune suppression or immune toleration, whereby proliferation of CD4+ CD25+ regulatory T cells is stimulated; and
   infusing an antigen-presenting dendritic cell into the mammal.

3. A method of stimulating the proliferation of CD4+ CD25+ regulatory T cells in a diabetic mammal, comprising:
   administering an effective amount of reagent cells comprising 4-1BBL-Fc on their surfaces to a diabetic mammal in need of immune suppression or immune toleration, whereby proliferation of CD4+CD25+ regulatory T cells is stimulated; and
   immunizing the mammal with an antigen.

4. A method of stimulating the proliferation of CD4$^+$ CD25$^+$ regulatory T cells in a diabetic mammal, comprising:

administering an effective amount of reagent cells comprising 4-1BBL-Fc on their surfaces to a diabetic mammal in need of immune suppression or immune toleration, whereby proliferation of CD4$^+$CD25$^+$ regulatory T cells is stimulated; and infusing an antigen-presenting dendritic cell into the mammal.

5. The method of claim 1 or 2 wherein the soluble 4-1BBL is a fusion protein with IgG-Fc.

6. The method of claim 1 or 2 wherein the mammal is a human.

7. The method of claim 1 or 2 wherein the mammal has induced auto-immune diabetes.

8. The method of claim 1 or 2 wherein anti-CD3 monoclonal antibody is also administered to the mammal.

9. The method of claim 3 or 4 wherein the mammal is a human.

10. The method of claim 3 or 4 wherein the mammal has induced auto-immune diabetes.

* * * * *